US006843800B1

(12) United States Patent
Dobak, III

(10) Patent No.: US 6,843,800 B1
(45) Date of Patent: Jan. 18, 2005

(54) PATIENT TEMPERATURE REGULATION METHOD AND APPARATUS

(75) Inventor: John D. Dobak, III, La Jolla, CA (US)

(73) Assignee: Innercool Therapies, Inc., San Diego, CA (US)

(*) Notice: Subject to any disclaimer, the term of this patent is extended or adjusted under 35 U.S.C. 154(b) by 0 days.

(21) Appl. No.: 09/373,112

(22) Filed: Aug. 11, 1999

Related U.S. Application Data

(63) Continuation-in-part of application No. 09/292,532, filed on Apr. 15, 1999, now abandoned, which is a continuation-in-part of application No. 09/215,058, filed on Dec. 16, 1998, now Pat. No. 6,261,312, which is a continuation-in-part of application No. 09/211,076, filed on Dec. 14, 1998, which is a continuation of application No. 09/103,342, filed on Jun. 23, 1998, now Pat. No. 6,096,068, which is a continuation-in-part of application No. 09/052,545, filed on Mar. 31, 1998, now Pat. No. 6,231,595, which is a continuation-in-part of application No. 09/847,012, filed on Mar. 24, 1998, now Pat. No. 5,957,963, which is a continuation-in-part of application No. 09/012,287, filed on Jan. 23, 1998, now Pat. No. 6,051,019.

(51) Int. Cl.$^7$ .................................................. A61F 7/00

(52) U.S. Cl. ...................................... 607/105; 607/113

(58) Field of Search .......................... 607/96, 104, 105, 607/106, 113; 606/20–24

(56) References Cited

U.S. PATENT DOCUMENTS

| 1,011,606 A | 12/1911 | Fulton |
|---|---|---|
| 2,308,484 A | 1/1943 | Auzin et al. |
| 2,374,609 A | 4/1945 | McCollum |
| 2,615,686 A | 10/1952 | Davidson |
| 2,672,032 A | 3/1954 | Towse |
| 2,913,009 A | 11/1959 | Kuthe |
| 3,298,371 A | 1/1967 | Lee |
| 3,425,419 A | 2/1969 | Dato |
| 3,504,674 A | 4/1970 | Swenson et al. |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,153,048 A | 5/1979 | Magrini |
| 4,190,033 A | 2/1980 | Foti |
| 4,231,425 A | 11/1980 | Engstrom |
| 4,275,734 A | 6/1981 | Mitchiner |

(List continued on next page.)

FOREIGN PATENT DOCUMENTS

| EP | 0655225 A1 | 5/1993 |
|---|---|---|
| EP | 0 664 990 | 11/1997 |
| EP | 1205167 A2 | 5/2002 |

(List continued on next page.)

OTHER PUBLICATIONS

Ikeda, Takahiko et al., "The Effect of Opioids on Thermoregulatory Responses in Humans and the Special Anti-shivering Action of Meperidine," *Annals New York Academy of Sciences*, Mar. 15, 1997,vol. 813, pp. 792–798.

Terasako, K. et al., "Comparison between pentazocine, pethidine ad placebo in the treatment of post–anesthetic shivering," *Acta Anaethesiol Scnd* 2000; 44: pp. 311–312.

Mercadante, Sebastiano et al., "Effect of Clonidine on Postpartum Shivering After Epidural Analgesia: A Randomized, Controlled, Double–Blind Study," *Journal of Pain and Symptom Managemnt*, vol. 9, No. 5, Jul. 1994, pp. 294–297.

(List continued on next page.)

Primary Examiner—Rosiland Rollins
(74) Attorney, Agent, or Firm—Karin L. Williams; Mayer Fortkort & Williams; Mark D. Wieczorek

(57) ABSTRACT

A device and method for providing body cooling. The cooling device applies cooling to blood flowing in a vena cavae that is then distributed throughout the body. The cooling can be assisted by use of thermoregulatory drugs or warming devices to prevent shivering and vasoconstriction.

16 Claims, 9 Drawing Sheets

U.S. PATENT DOCUMENTS

| | | |
|---|---|---|
| 4,298,006 A | 11/1981 | Parks |
| 4,318,722 A | 3/1982 | Altman |
| 4,427,009 A | 1/1984 | Wells et al. |
| 4,445,500 A | 5/1984 | Osterholm |
| 4,483,341 A | 11/1984 | Witteles |
| 4,502,286 A | 3/1985 | Okada et al. |
| 4,569,355 A | 2/1986 | Bitterly |
| 4,581,017 A | 4/1986 | Sahota |
| 4,655,746 A | 4/1987 | Daniels et al. |
| 4,672,962 A | 6/1987 | Hershenson |
| 4,748,979 A | 6/1988 | Hershenson |
| 4,750,493 A | 6/1988 | Brader |
| 4,762,130 A | 8/1988 | Fogarty et al. |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,964,409 A | 10/1990 | Tremulis |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,041,089 A | 8/1991 | Mueller et al. |
| 5,078,713 A | 1/1992 | Varney |
| 5,092,841 A | 3/1992 | Spears |
| 5,106,360 A | 4/1992 | Ishwara et al. |
| 5,108,390 A | 4/1992 | Potocky et al. |
| 5,110,721 A | 5/1992 | Anaise et al. |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,306,261 A | 4/1994 | Alliger et al. |
| 5,310,440 A | 5/1994 | Zingher |
| 5,334,193 A | 8/1994 | Nardella |
| 5,342,301 A | 8/1994 | Saab |
| 5,344,436 A | 9/1994 | Fontenot et al. |
| 5,365,750 A | 11/1994 | Greenthal |
| 5,368,591 A | 11/1994 | Lennox et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Allger et al. |
| 5,462,521 A | 10/1995 | Brucker et al. |
| 5,486,204 A | 1/1996 | Clifton |
| 5,486,208 A | 1/1996 | Ginsburg |
| 5,531,776 A | 7/1996 | Ward et al. |
| 5,558,644 A | 9/1996 | Boyd et al. |
| 5,573,532 A | 11/1996 | Chang et al. |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,624,392 A | 4/1997 | Saab |
| 5,643,197 A | 7/1997 | Brucker et al. |
| 5,647,051 A | 7/1997 | Neer |
| 5,713,941 A | 2/1998 | Robins et al. |
| 5,716,386 A | 2/1998 | Ward et al. |
| 5,735,809 A | 4/1998 | Gorsuch |
| 5,797,878 A | 8/1998 | Bleam |
| 5,800,480 A | 9/1998 | Augustine et al. |
| 5,807,391 A | 9/1998 | Wijkamp |
| 5,824,030 A | 10/1998 | Yang et al. |
| 5,827,222 A | 10/1998 | Klatz et al. |
| 5,827,237 A | 10/1998 | Macoviak et al. |
| 5,833,671 A | 11/1998 | Macoviak et al. |
| 5,837,003 A | 11/1998 | Ginsburg |
| 5,861,021 A | 1/1999 | Thome et al. |
| 5,871,526 A | 2/1999 | Gibbs et al. |
| 5,873,835 A | 2/1999 | Hastings et al. |
| 5,879,329 A | 3/1999 | Ginsburg |
| 5,899,899 A * | 5/1999 | Arless et al. .................. 606/20 |
| 5,902,268 A | 5/1999 | Saab |
| 5,913,885 A | 6/1999 | Klatz et al. |
| 5,913,886 A | 6/1999 | Soloman |
| 5,916,242 A | 6/1999 | Schwartz |
| 5,957,963 A | 9/1999 | Dobak, III |
| 5,989,238 A | 11/1999 | Ginsburg |
| 6,019,783 A | 2/2000 | Philips et al. |
| 6,033,383 A | 3/2000 | Ginsburg |
| 6,042,559 A | 3/2000 | Dobak, III |
| 6,051,019 A | 4/2000 | Dobak, III |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A | 11/2000 | Noda et al. |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,224,624 B1 | 5/2001 | Lasheras et al. |
| 6,231,595 B1 | 5/2001 | Dobak, III |
| 6,235,048 B1 | 5/2001 | Dobak, III |
| 6,245,095 B1 | 6/2001 | Dobak, III et al. |
| 6,402,775 B1 | 6/2002 | Bieberich |
| 6,416,533 B1 | 7/2002 | Gobin et al. |
| 6,419,643 B1 | 7/2002 | Shimada et al. |
| 6,432,124 B1 | 8/2002 | Worthen et al. |
| 6,582,457 B2 | 6/2003 | Dae et al. .................. 607/113 |
| 2001/0002442 A1 | 5/2001 | Dobak, III |
| 2001/0005791 A1 * | 6/2001 | Ginsburg et al. ............ 607/106 |
| 2002/0066458 A1 | 6/2002 | Aliberto et al. |
| 2002/0068877 A1 | 6/2002 | Abramovitch et al. |
| 2002/0091429 A1 | 7/2002 | Dobak, III |
| 2002/0091430 A1 | 7/2002 | Dobak, III |
| 2002/0103519 A1 | 8/2002 | Dobak, III et al. |
| 2002/0107558 A1 | 8/2002 | Clifton |
| 2002/0111657 A1 | 8/2002 | Dae et al. |

FOREIGN PATENT DOCUMENTS

| | | |
|---|---|---|
| EP | 1029520 B1 | 8/2002 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |

| | | |
|---|---|---|
| WO | WO 97/01374 | 1/1997 |
| WO | WO 97/25011 | 7/1997 |
| WO | WO 98/26831 | 6/1998 |
| WO | WO 98/31312 | 7/1998 |
| WO | WO 99/37226 | 7/1999 |
| WO | WO 99/48449 | 9/1999 |
| WO | WO 99/66970 | 12/1999 |
| WO | WO99/66971 | 12/1999 |
| WO | WO 00/09054 | 2/2000 |
| WO | WO 00/10494 | 3/2000 |
| WO | WO 0038601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 A2 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13837 | 3/2001 |

OTHER PUBLICATIONS

Coimbra, Cicero et al., "Long–lasting Neuroprotective Effect of Postischemic Hypothermia and Treatment With an Anti–inflammatory/Antipyretic Drug," *Stroke*, vol. 27, No. 9, Sep. 1996, pp. 1578–1584.

Casey, William F. et al., "Intravenous meperidine for control of shivering during Caesarean section under epidural anaesthesia," *Can J Anaesth 1988*, vol. 35:2, pp. 128–133.

Chan, Anne Miu Han et al., "Control of shivering under regional anesthesia in obstetric patients with tramadol," *Can J Anesth 1999*, vol. 46:3, pp. 253–258.

Crossley, A.W.A., "Six months of shivering in a district general hospital," Anaesthesia, 1992, vol. 47, pp. 845–848.

Cruise, Charles et al., "Comparison of meperidine and pancuronium for the treatment of shivering after cardiac surgery," *Can J Anaesth 1992*, vol. 39:6, pp. 563–568.

Delaunay, L. et al., "Clonidine Decreases Postoperative Oxygen Consumption In Patients Recovering From General Anaesthesia," British Journal of Anaesthesia 1991, vol. 67, pp. 397–401.

DeWitte, J et al., "Tramadol in the treatment of postanesthetic shivering," *Acta Anaesthesiol Scand* 1997, vol. 41, pp. 506–510.

DeWitte Jan L. et al., "Tramadol Reduces the Sweating, Vasoconstricton, and Shivering Thresholds," *Anesth Analg 1998*, vol. 87, pp. 173–179.

Horn, Ernst–Peter et al., "Late Intraoperative Clonidine Administration Prevents Postanesthetic Shivering After Total Intravenous or Volatile Anesthesia," *Anesth Analog 1997*, vol. 84, pp. 613–617.

Joris, Jean, "Clonidine and Ketanserin Both Are Effective Treatment for Postanesthetic Shivering," Anesthesiology, vol. 79, No. 3, Sep. 1993, pp. 532–539.

Nicolaou, George et al., "Clonidine decreases vasoconstriction and shivering thresholds, without affecting the sweating threshold," *Can J Anaesth 1997*, vol. 44:6, pp. 636–642.

Sladen, Robert N. et al., "Comparison of Vecuronium and Meperidine on the Clinical and Metabolic Effects of Shivering After Hypothermic Cardiopulmonary Bypass," *Journal of Cardiothoracic and Vascular Anesthesia*, vol. 9, No. 2, Apr. 1995, pp. 147–153.

Vanderstappen, I. et al., "The effect of prophylactic clonidine on postoperative shivering," *Anaesthesia*, 1996, vol. 51, pp. 351–355.

Vogelsang, Joan et al., "Butorphanol Tartrate (Stadol) Relieves Postanesthesia Shaking More Effectively Than Meperidine (Demerol) or Morphine," *Journal of Post Anesthesia Nursing*, vol. 7, No. 2, Apr. 1992, pp. 94–100.

Wang, Jhi–Joung et al., "A Comparison Among Nalbuphine, Meperidine, and Placebo for Treating Postanesthetic Shivering," *Anesth Analg 1999*, vol. 88, pp. 686–689.

Yang, Chen–Hsien et al., "Effect of Intravenous Clonidine on Prevention of Postepidural Shivering," *Acta Anaesthesiol Sin*, vol. 31, 1993, pp. 121–126.

Zweifler, Richard M. et al., "Thermoregulatory Vasoconstriction and Shivering Impede Therapeutic Hypothermia in Acute Ischemic Stroke Patients," *Journal of Stroke and Cerebrovascular Diseases*, vol. 6, No. 2, 1996, pp. 100–104.

Wrench, I.J. et al., "Comparison between alfentanil, pethidine and placebo in the treatment of postanaesthetic shivering," British Journal of Anaesthesia 1997, vol. 79, pp. 541–542.

Ambrus; *The Biphasic Nature and Temperature Dependence of the Activation of Human Plasminogen by Urokinase*; May 1979; pp. 339–347; Research Communications in Chemical Pathology and Pharmacology, vol. 24, No. 2.

Bigelo; *Hypothermia, Its Possible Role in Cardiac Surgery*, Nov. 1959, pp. 849–866; Annals of Surgery, vol. 132, No. 5.

Cheatle; *Cryostripping the Long and Short Saphenous Veins*; Jan. 1993; one page; Br. J. Surg., vol. 80.

Dexter; *Blood Warms as It Blows Retrograde from a Femoral Cannulation Site to the Carotid Artery During Cardiopulmonary Bypass*; Nov. 1994; pp. 393–397; Perfusion, vol. 9, No. 6.

Gillinov; *Superior Cerebral Protection with Profound Hypothermia During Circulatory Arrest*; Nov. 1992; pp. 1432–1439; Ann. Thorac. Surg., vol. 55.

Higazi; *The Effect of Ultrasonic Irradiation and Temperature on Fibrinolytic Activity in Vitro*; Sep. 1992; p. 251–253; Thrombosis Research, vol. 69, No. 2.

Iaizzo; *Facial Warming Increases the Threshold for Shivering*, 1999, Journal of Neurosurgical Anesthesiology, vol. 11, No. 4, pp. 231–239.

Imamaki; *Retrograde Cerebral Perfusion with Hypothermic Blood Provides Efficient Protection of the Brain*; Jul. 1995; pp. 325–333; Journal of Cardiac Surgery, vol. 10, No. 4, Part 1.

Jolin; *Management of a Giant Intracranial Aneurysm Using Surface–Heparinized Extracorporeal Circulation and Controlled Deep Hypothermic Low Flow Perfusion*; Aug. 1992; pp. 756–760; Acta Anaesthesiologica Scandinavia.

Jos R.C. Jansen, Ph.D., et al. (1997) *Near continuous cardiac output by thermodilution*. Journal of Clinical Monitoring 13:233–239.

Kimoto; *Open Heart Surgery under Direct Vision with the Aid of Brain–Cooling by Irrigation*; Jul. 1995; pp. 592–603; Surgery, vol. 39, No. 4.

Marekovic, Z.; *Abstract of Renal Hypothermia in Situ by Venous Passages: Experimental Work on Drugs*; 1980; Eur Urol 6(2); 1 page.

Meden; *Effect of Hypothermia and Delayed Thrombolysis in a Rat Embolic Stroke Model*; Dec. 1993; pp. 91–98; Acta Neurologica Scandinavica.

Meden; *The Influence of Body Temperature on Infarct Volume and Thrombolytic Therapy in a Rat Embolic Stroke Model*; Feb. 1994; pp. 131–138; Brain Research; vol. 647.

Milleret, Rene; *La cryo–chirurgie danes les varices des mimbres inferieurs*; Angiologie; Supplement au No. 110.

Milleret; Abstract of *Cryosclerosis of the Saphenous Veins in Varicose Reflux in the Obese and Elderly*; 10.1981; one page; Phlebologie, vol. 34, No. 4.

Parkins; *Brain Cooling in the Prevention of Brain Damage During Periods of Circulatory Occlusion in Dogs*; Apr. 1954; pp. 284–289; Annals of Surgery, vol. 140, No. 3.

Piepgras; *Rapid Active Internal Core Cooling for Induction of Moderate Hypothermia in Head Injury by Use of an Extracorporeal Heat Exchanger*, Feb. 1998; pp. 311–318; Neurosurgery, vol. 42, No. 2.

Rijken; *Plasminogen Activation at Low Temperatures in Plasma Samples Containing Therapeutic Concnetrations of Tissue–Type Plasminogen Activator or Other Thrombolytic Agents*; Oct. 1989; pp. 47–52; place of publication unknown.

Schwartz, A.E. et al., (1996); *Isolated cerebral hypothermia by single carotid artery perfusion of extracorporeally cooled blood in baboons*; Neurosurgery 39(3):577–580.

Schwartz; *Cerebral Blood Flow during Low–flow Hypothermic Cardiopulmonary Bypass in Baboons*; Jun. 1994; pp. 959–964; Anesthesiology, vol. 81, No. 4.

Schwartz; *Selective Cerebral Hypothermia by Means of Transfemoral Internal Carotid Artery Catheterization*; May 1996; pp. 571–572; Radiology, vol. 201, No. 2.

Steen;*The Detrimental Effects of Prolonged Hypothermia and Rewarming in the Dog*; Aug. 1979; pp. 224–230; Anesthesiology, vol. 52, No. 3.

Vandam; *Hyothermia*; Sep. 1959; pp. 546–553; The New England Jouranl of Medicine.

White; *Cerebral Hypothermia and Circulatory Arrest*; Jul. 1978; pp. 450–458; Mayo Clinic Proceedings, vol. 53.

Yenari; *Thrombolysis with Tissue Plasminogen Activator (TPA) is Temperature Dependent*; Jul. 1994; pp.475–481; Thrombosis Research, vol. 77, No. 5.

Yoshihara; *Changes in Coagulation and Fibrinolysis Occurring in Dogs during Hypothermia*; Aug. 1984; pp. 503–512; Thrombosis Research, vol. 37, No. 4.

Zarins; *Circulation in Profound Hypothermia*; Nov. 1972; pp. 97–104; Journal of Surgical Research, vol. 14, N. 2.

Cheng, C. et al. (1995), "Increasing Mean Skin Temperature Linearly Reduces the Core–Temperature Thresholds for Vasoconstriction and Shivering in Humans," *Anesthesiology* 82(5):1160–1168, May.

Giuffre, M. et al. (1991), "Rewarming Postoperative Patients: Lights, Blankets, or Forced Warm Air," *Journal of Post Anesthesia Nursing*, 6(6):386–393, Dec.

Alfonsi, P., D. I. Sessler, B. Du Manoir, J–C. Levron, J–P. Le Moing, M. Chauvin, "The Effects of Meperidine and Sufentanil on the Shivering Threshold in Postoperative Patients," *Anesthesiology*, Jul. 1998, 89(1):43–48.

Deklunder, G., M. Dauzat, J–L. Lecroart, J–J. Hauser, and Y. Houdas, "Influence of Ventilation of the Face on Thermoregulation in Man during Hyper– and Hypothermia," *Eur. J. Appl. Physiol.*, 1991, 62:342–348.

Gentilello, L. M., "Advances in the Management of Hypothermia," *Horizons in Trauma Surgery*, Apr. 1995, 75(2):243–256.

Haley, E. C. et al. "A Randomized Trial of Tirilazad Mesylate in Patients with Acute Stroke (RANTTAS)," *Stroke*, 1996, 27(9):1453–1458.

Keegan, M. T. et al., "Shivering Complicating the Treatment of Neurologically Impaired Surgical and Intensive Care Unit Patients," *Anesthesiology*, Sep. 1999, 91(3):874–876.

Villamaria, F. J., C. E. Baisden, A. Hillis, M. H. Rajab, and P. A. Rinaldi, "Forced–Air Warming is No More Effective than Conventional Methods for Raising Postoperative Core Temperature After Caridac Surgery," *Journ. Cardiothoracic and Vascular Anesth.*, Oct. 1997, 11(6):708–711.

Gruffin, Anita, et al.; "Shivering Following Cardiac Surgery: Hemodynamic Changes and Reversal."; Journal of Cardiothoracic Anesthesia; (Feb. 1987); pp. 24–28; vol. 1, No. 1.

Kurz, Martin, et al.; "Naloxone, Meperidine, and Shivering."; Anesthesiology; (Dec. 1983); pp. 1193–1201; V. 79; No. 6.

Sessler, Daniel I.; "Mild Perioperative Hypothermia"; The New England Journal of Medicine; pp. 1730–1737; 336:1730–1737; (Jun. 12, 1997).

Zweifler, R. M. and D. I. Sessler, "Thermoregulatory Vasoconstriction and Shivering Impede Therapeutic Hypothermia in Acute Ischemic Stroke Patients," *Journ. Stroke and Cerebrovascular Diseases*, V. 6, No. 2, 1996: pp. 100–104.

Cabanac, M.; "Selective brain cooling and thermoregulatory set–point:"; Journal of Basic & Clinical Physiology & Pharmacology; Department de Physiologie, Faculte de medecine, Universite Laval, Quebec QC, Canada G1K 7P4; Freund Publishing House Ltd., 1998; pp. 3–13.

Capongna, G., et al.; "IV clonidine for post–extradural shibering in parturients: a preliminary study"; British Journal of Anaesthesia; 1993; 71:294–295.

Sharkey, A., et al. ; "Inhibition of postanesthestic shivering with radiant heat"; Anesthesiology; vol. 66; No. 2; Feb. 1987; pp. 249–252.

Lennon, Robert L., et al.; "Evaluation of a Forced–Air for Warming Hypothermic Postoperative Patients"; Anesth Analg; vol. 70; pp. 424–427; 1990.

Grigore, Alina, et al., "Temperature Regulation and Manipulation During Surgery and Anesthesia", Anesthesiology Online Journal (May 1998); available at: http://www.anesthesiologyonline.com/article/onepage.cfm?chapter_id=11&journal=1.

Dicker, Andrea, et al., "Halothane Selectively Inhibits Nonshivering Thermogenesis"; Anethesiology, vol. 82, No. 2, pp. 491–501 (Feb. 1995).

Plattner, Olga, et al., "Lack of Nonshivering Thermogenesis in Infants Anesthetrized with Fentanyl and Propofol", Anesthesiology, vol. 86, No. 45 (Apr. 1997).

Fulbrook, Paul, "Core Body Temperature Measurement: a Comparison of Axilla, Tympanic Membrane and Pulmonary Artery Blood Temperature", Intensive and Criticial Care Nursing (1997) 13 (pp. 266–272).

Matsukawa, T., et al., "Comparison of Distal Oesophageal Temperature with "Deep" and Tracheal Temperatures", Canadian Journal of Anaesthesia, vol. 44, No. 4, pp. 433–438(1997).

Behmann, F.W.; "Regulation of heat production in experimental hypothermia of homothermal animals"; Naunyn Schmiedebergs Arch Exp Pathol Pharmakol; 228 (1–2): 126–128 (1956). (German article with English translation).

* cited by examiner

PATIENT TEMPERATURE REGULATION METHOD AND APPARATUS

CROSS REFERENCE TO RELATED APPLICATIONS

This is a continuation-in-part patent application of co-pending U.S. patent application Ser. No. 09/215,038 filed on Dec. 16, 1998, and entitled "INFLATABLE CATHETER FOR SELECTIVE ORGAN HEATING AND COOLING AND METHOD OF USING THE SAME" and of co-pending U.S. patent application Ser. No. 09/292,532, filed on Apr. 15, 1999 now abandoned, and entitled "Isolated Selective Organ Cooling Method and Apparatus", the latter of which is a continuation-in-part patent application of U.S. patent application Ser. No. 09/052,545 filed on Mar. 31, 1998, and entitled "Circulating Fluid Hypothermia Method and Apparatus" now as U.S. Pat. No. 6,231,595 and U.S. patent application Ser. No. 09/103,342, filed on Jun. 23, 1998, and entitled "Selective Organ Cooling Catheter and Method of Using the Same", now U.S. Pat. No. 6,096,068, which is a continuation-in-part patent application of U.S. patent application Ser. No. 09/047,012 filed on Mar. 24, 1998, and entitled "Selective Organ Hypothermia Method and Apparatus", now U.S. Pat. No. 5,957,963, which is a continuation-in-part patent application of U.S. patent application Ser. No. 09/012,287 filed on Jan. 23, 1998, and entitled "Selective Organ Hypothermia Method and Apparatus", now U.S. Pat. No. 6,051,019.

STATEMENT REGARDING FEDERALLY SPONSORED RESEARCH OR DEVELOPMENT

Not applicable

BACKGROUND OF THE INVENTION

1. Field of the Invention

The present invention relates generally to the lowering and control of the temperature of the human body. More particularly, the invention relates to a method and intravascular apparatus for cooling the body without the adverse consequences associated with prior methods of total body cooling. The invention also relates to a method and intravascular apparatus for cooling the body without causing thermoregulatory suppression of the cooling.

2. Background Information

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as a mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. The currently-employed techniques and devices used to cause total body hypothermia lead to various side effects. In addition to the undesirable side effects, present methods of administering total body hypothermia are cumbersome.

Catheters have been developed which are inserted into the bloodstream of the patent in order to induce total body hypothermia. For example, U.S. Pat. No. 3,425,419 to Dato describes a method and apparatus of lowering and raising the temperature of the human body. Dato induces moderate hypothermia in a patent using a rigid metallic catheter. The catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. Thus, the Dato device cools along the length of a very elongated device. Use of the Dato device is highly cumbersome due to its size and lack of flexibility.

U.S. Pat. No. 5,837,003 to Ginsburg also discloses a method and apparatus for controlling a patient's body temperature. In this technique, a flexible catheter is inserted into the femoral artery or vein or the jugular vein. The catheter may be in the form of a balloon to allow an enhanced surface area for heat transfer. A thermally conductive metal foil may be used as part of a heat-absorbing surface. This device fails to disclose or teach use of any ability to enhance heat transfer. In addition, the disclosed device fails to disclose temperature regulation.

Therefore, a practical method and apparatus that lowers and controls the temperature of the human body satisfies a long-felt need.

BRIEF SUMMARY OF THE INVENTION

In one aspect, the apparatus of the present invention can include a heat transfer element that can be used to apply cooling to the blood flowing in a large vein feeding the heat. An optional heating element may be used to supply warming to a portion of the remainder of the body to provide comfort to the patient and to allow a low target hypothermic temperature to be achieved. The heating element may be applied before or after a target temperature is achieved. The warming operation can be accomplished by means of local heating of the vein or artery with an external heat applicator or by means of substantially whole body warming with a heating blanket. The warming operation can be accomplished per se or in combination with thermoregulatory drugs.

The heat transfer element, by way of example only, includes first and second elongated, articulated segments, each segment having a mixing-inducing exterior surface. A flexible joint can connect the first and second elongated segments. An inner lumen may be disposed within the first and second elongated segments and is capable of transporting a pressurized working fluid to a distal end of the first elongated segment. In addition, the first and second elongated segments may have a mixing-inducing interior surface for inducing mixing within the pressurized working fluid. The mixing-inducing exterior surface may be adapted to induce mixing within a blood flow when placed within an artery or vein. In one embodiment, the flexible joint includes a bellows section that also allows for axial compression of the heat transfer element as well as for enhanced flexibility. In alternative embodiments, the bellows section may be replaced with flexible tubing such as small cylindrical polymer connecting tubes.

In one embodiment, the mixing-inducing exterior surfaces of the heat transfer element include one or more helical grooves and ridges. Adjacent segments of the heat transfer element can be oppositely spiraled to increase mixing. For instance, the first elongated heat transfer segment may include one or more helical ridges having a counter-clockwise twist, while the second elongated heat transfer segment includes one or more helical ridges having a clockwise twist. Alternatively, of course, the first elongated heat transfer segment may include one or more clockwise helical ridges, and the second elongated heat transfer segment may include one or more counter-clockwise helical ridges. The first and second elongated, articulated segments may be formed from highly conductive materials such as metals.

The heat transfer device may also have a supply catheter with an inner catheter lumen coupled to the inner lumen within the first and second elongated heat transfer segments. A working fluid supply configured to dispense the pressurized working fluid may be coupled to the inner catheter lumen or alternatively to the supply catheter. The working fluid supply may be configured to produce the pressurized working fluid at a temperature of about 0° C. and at a pressure below about 5 atmospheres of pressure.

In yet another alternative embodiment, the heat transfer device may have three or more elongated, articulated, heat transfer segments each having a mixing-inducing exterior surface, with additional flexible joints connecting the additional elongated heat transfer segments. In one such embodiment, by way of example only, the first and third elongated heat transfer segments may include clockwise helical ridges, and the second elongated heat transfer segment may include one or more counter-clockwise helical ridges. Alternatively, of course, the first and third elongated heat transfer segments may include counter-clockwise helical ridges, and the second elongated heat transfer segment may include one or more clockwise helical ridges.

The mixture-inducing exterior surface of the heat transfer element may optionally include a surface coating or treatment to inhibit clot formation. A surface coating may also be used to provide a degree of lubricity to the heat transfer element and its associated catheter.

The present invention is also directed to a method of inducing hypothermia in the body by inserting a flexible, conductive cooling element into a vein that is in pressure communication with the heart, e.g., the superior or inferior vena cavae or both. The vena cavae may be accessed via known techniques from the jugular vein or from the subclavian or femoral veins, for example. The heat transfer element in one or both vena cavae may then cool virtually all the blood being returned to the heart. The cooled blood enters the right atrium at which point the same is pumped through the right ventrical and into the pulmonary artery to the lungs where the same is oxygenated. Due to the heat capacity of the lungs, the blood does not appreciably warm during oxygenation. The cooled blood is returned to the heart and pumped to the entire body via the aorta. Thus, cooled blood may be delivered indirectly to a chosen organ such as the brain. This indirect cooling is especially effective as high blood flow organs such as the heart and brain are preferentially supplied blood by the vasculature. A warming blanket or other warming device may be applied to portions of the body to provide conformt to the patient and to inhibit thermoregulatory responses such as vasoconstriction. Thermoregulatory drugs may also be so provided for this reason.

The method further includes circulating a working fluid through the flexible, conductive cooling element in order to lower the temperature of the blood in the vena cava. The flexible, conductive heat transfer element preferably absorbs more than about 150 or 300 Watts of heat.

The method may also include inducing mixing within the free stream blood flow within the vena cava. It is noted that a degree of turbulence or mixing is generally present within the vena cava anyway. The step of circulating may include inducing mixing in the flow of the working fluid through the flexible, conductive heat transfer element. The pressure of the working fluid may be maintained below about 5 atmospheres of pressure.

The present invention also envisions a method for inducing therapeutic hypothermia in the body of a patient which includes introducing a catheter, with a cooling element, into a vena cava supplying the heart, the catheter having a diameter of about 18 mm or less, inducing mixing in blood flowing over the cooling element, the lowering the temperature of the cooling element to remove heat from the blood to cool the blood. In one embodiment, the cooling step removes at least about 150 Watts of heat from the blood. In another embodiment, the cooling step removes at least about 300 Watts of heat from the blood.

The mixing induced may result in a Nusselt number enhancement of the flow of between about 5 and 80.

In another aspect of the method, the invention is directed to a method of lowering the temperature of the body while prohibiting intervention of the body's thermoregulatory responses. Steps of the method may include delivering a drug to lower the thermoregulatory setpoint of the body such that thermoregulatory responses, including shivering and vasoconstriction, are not triggered above a certain temperature, wherein the certain temperature is lower than normal body temperature. The temperature of the blood in a major vein such as the vena cava is then lowered to induce hypothermia in the body. The thermoregulatory drugs provide patient comfort. If even lower body temperatures are desired or required, heating blankets may be provided to further ensure patient comfort. Generally, for one degree of body core cooling, the heating blanket should be 5° C. above the skin temperature to provide patient comfort. However, the temperature of the blanket should generally not exceed 42° C.

Advantages of the invention are numerous. Patients can be provided with the beneficial aspects of hypothermia without suffering the deleterious consequences of the prior art. The procedure can be administered safely and easily. Numerous cardiac and neural settings can benefit by the hypothermic therapy. For example, ischemia and restenosis can be minimized. Other advantages will be understood from the following.

The novel features of this invention, as well as the invention itself, will be best understood from the attached drawings, taken along with the following description, in which similar reference characters refer to similar parts, and in which:

DETAILED DESCRIPTION OF THE INVENTION

OVERVIEW

A one or two-step process and a one or two-piece device may be employed to intravascularly lower the temperature of a body in order to induce therapeutic hypothermia. A cooling element may be placed in a high-flow being such as the vena cavae to absorb heat from the blood flowing into the heart. This transfer of heat causes a cooling of the blood flowing through the heart and thus throughout the vasculature. Such a method and device may therapeutically be used to induce an artificial state of hypothermia.

A heat transfer element that systemically cools blood should be capable of providing the necessary heat transfer rate to produce the desired cooling effect throughout the vasculature. This may be up to or greater than 300 watts, and is at least partially dependent on the mass of the patient and the rate of blood flow. Surface features may be employed on the heat transfer element to enhance the heat transfer rate. The surface features and other components of the heat transfer element are described in more detail below.

One problem with hypothermia as a therapy is that the patient's thermoregulatory defenses initiate, attempting to defeat the hypothermia. Methods and devices may be used to lessen the thermoregulatory response. For example, a heating blanket may cover the patient. In this way, the patient may be made more comfortable. Thermoregulatory drugs may also be employed to lower the trigger point at which the patient's thermoregulatory system begins to initiate defenses. Such drugs are described in more detail below. A method employing thermoregulatory drugs, heating blankets, and heat transfer elements is also disclosed below.

ANATOMICAL PLACEMENT

The internal jugular vein is the vein that directly drains the brain. The external jugular joins the internal jugular at the base of the neck. The internal jugular veins join the subclavin veins to form the brachiocephalic veins that in turn drain into the superior vena cava. The superior vena cava drains into the right atrium of the heart as may be seen by referring ahead to FIG. 9. The superior vena cava supplies blood to the heart from the upper part of the body.

A cooling element may be placed into the superior vena cava, inferior vena cava, or otherwise into a vein which feeds into the superior vena cava or otherwise into the heat to cool the body. A physician percutaneously places the catheter into the subclavin or internal or external jugular veins to access the superior vena cava. The blood, cooled by the heat transfer element, may be processed by the heart and provided to the body in oxygenated form to be used as a conductive medium to cool the body. The lungs have a fairly low heat capacity, and thus the lungs do not cause appreciable rewarming of the flowing blood.

Figure 10:
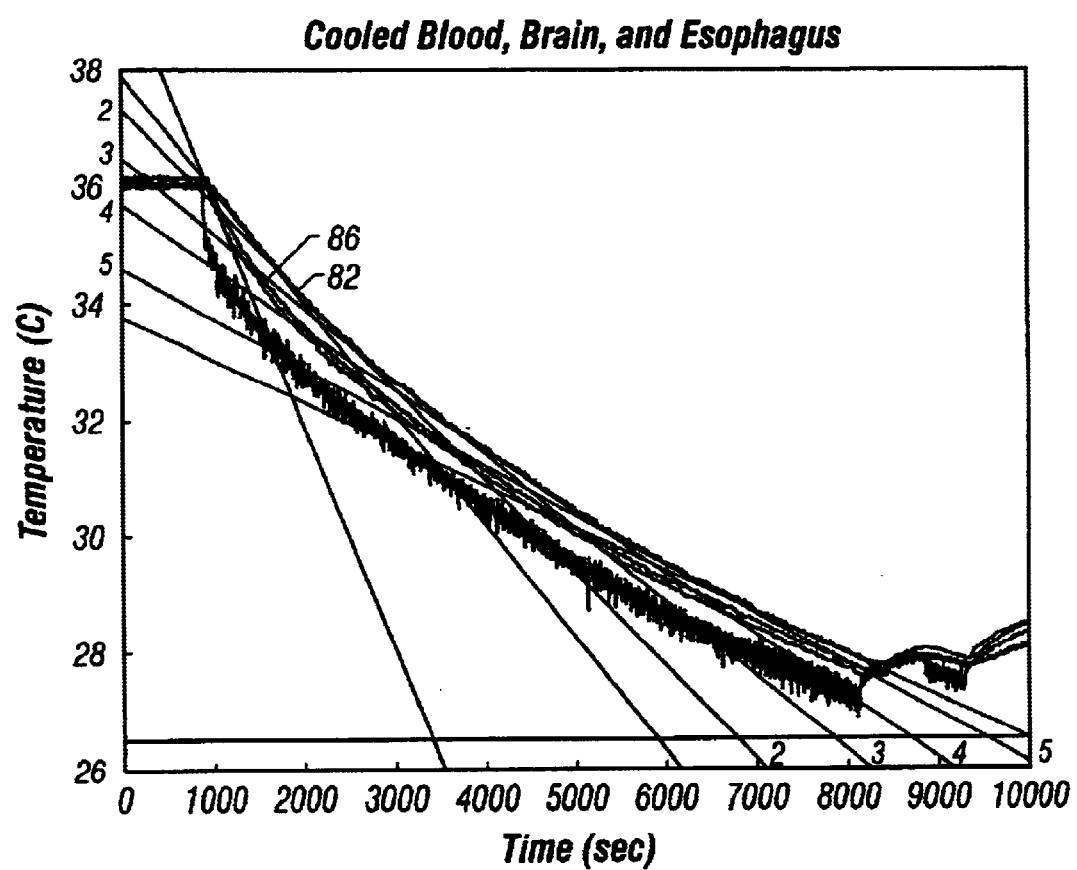
FIG. 10 is a graph showing preferential cooling of the high flow organs of the body under a hypothermic therapy.

The vasculature by its very nature provides preferential blood flow to the high blood flow organs such as the brain and the heart. Thus, these organs are preferentially cooled by such a procedure as is also shown experimentally in FIG. 10. FIG. 10 is a graph of measured temperature plotted versus cooling time. This graph show the effect of placing a cooling element in the superior vena cava of a sheep. The core body temperature as measured by an esophageal probe is shown by curve 82. The brain temperature is shown by curve 86. The brain temperature is seen to decrease more rapidly than the core body temperature throughout the experiment. The inventors believe this effect to be due to the preferential supply of blood provided to the brain and heart. This effect may be even more pronounced if thermoregulatory effects, such as vasoconstriction, occur that tend to focus blood supply to the core vascular system and away from the peripheral vascular system.

HEAT TRANSFER

When a heat transfer element is inserted approximately coaxially into an artery or vein, the primary mechanism of heat transfer between the surface of the heat transfer element and the blood is forced convection. Convection relies upon the movement of fluid to transfer heat. Forced convection results when an external force causes motion within the fluid. In the case of arterial or venous flow, the beating heart causes the motion of the blood around the heat transfer element.

The magnitude of the heat transfer rate is proportional to the surface area of the heat transfer element, the temperature differential, and the heat transfer coefficient of the heat transfer element.

The receiving artery or vein into which the heat transfer element is placed has a limited diameter and length. Thus, the surface area of the heat transfer element must be limited to avoid significant obstruction of the artery or vein and to allow the heat transfer element to easily pass through the vascular system. For placement within the superior vena cava via the external jugular, the cross sectional diameter of the heat transfer element may be limited to about 5–6 mm, and its length may be limited to approximately 10–15 cm. For placement within the inferior vena cava, the cross sectional diameter of the heat transfer element may be limited to about 6–7 mm, and its length may be limited to approximately 25–35 cm.

Decreasing the surface temperature of the heat transfer element can increase the temperature differential. However, the minimum allowable surface temperature is limited by the characteristics of blood. Blood freezes at approximately 0° C. When the blood approaches freezing, ice emboli may form in the blood, which may lodge downstream, causing serious ischemic injury. Furthermore, reducing the temperature of the blood also increases its viscosity, which results in a small decrease in the value of the convection heat transfer coefficient. In addition, increased viscosity of the blood may result in an increase in the pressure drop within the artery, thus compromising the flow of blood to the brain. Given the above constraints, it is advantageous to limit the minimum allowable surface temperature of the cooling element to approximately 5° C. This results in a maximum temperature differential between the blood stream and the cooling element of approximately 32° C. For other physiological reasons, there are limits on the maximum allowable surface temperature of the warming element.

The mechanisms by which the value of the convection heat transfer coefficient may be increased are complex. However, it is well known that the convection heat transfer coefficient increases with the level of "mixing" or "turbulent" kinetic energy in the fluid flow. Thus it is advantageous to have blood flow with a high degree of mixing in contact with the heat transfer element.

The blood flow has a considerably more stable flux in the superior vena cava than in an artery. However, the blood flow in the superior vena cava still has a high degree of inherent mixing or turbulence. Reynolds numbers in the superior vena cava may range, for example, from 2,000 to 5,000. Thus, blood cooling in the superior vena cava may benefit from enhancing the level of mixing with the heat transfer element but this benefit may be substantially less than that caused by the inherent mixing.

BOUNDARY LAYERS

A thin boundary layer has been shown to form during the cardiac cycle. Boundary layers develop adjacent to the heat transfer element as well as next to the walls of the artery or vein. Each of these boundary layers has approximately the same thickness as the boundary layer that would have developed at the wall of the artery in the absence of the heat transfer element. The free stream flow region is developed in an annular ring around the heat transfer element. The heat transfer element used in such a vessel should reduce the formation of such viscous boundary layers.

HEAT TRANSFER ELEMENT CHARACTERISTICS AND DESCRIPTION

The intravascular heat transfer element should be flexible in order to be placed within the vena cavae or other veins or arteries. The flexibility of the heat transfer element is an important characteristic because the same is typically inserted into a vein such as the external jugular and accesses the superior vena cava by initially passing though a series of one or more branches. Further, the heat transfer element is ideally constructed form a highly thermally conductive material such as metal in order to facilitate heat transfer. The use of a highly thermally conductive material increases the heat transfer rate for a given temperature differential between the working fluid within the heat transfer element and the blood. This facilitates the use of a higher temperature coolant, or lower temperature warming fluid, within the heat transfer element, allowing safer working fluids, such as water or saline, to be used. Highly thermally conductive materials, such as metals, tend to be rigid. Therefore, the design of the heat transfer element should facilitate flexibility in an inherently inflexible material.

It is estimated that the cooling element should absorb at least about 300 Watts of heat when placed in the superior vena cava to lower the temperature of be body to between about 30° C. and 34° C. These temperatures are thought to be appropriate to obtain the benefits of hypothermia described above. The power removed determines how quickly the target temperature can be reached. For example, in a stroke therapy in which it is desired to lower brain temperature, the same may be lowered about 4° C. per hour in a 70 kg human upon removal of 300 Watts.

One embodiment of the invention uses a modular design. The design creates helical blood flow and produces a level of mixing in the blood flow by periodically forcing abrupt changes in the direction of the helical blood flow. The abrupt changes in flow direction are achieved through the use of a series of two or more heat transfer segments, each included of one or more helical ridges. The use of periodic abrupt changes in the helical direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent motion within the clothes-water slurry. These surface features also tend to increase the surface area of the heat transfer element, further enhancing heat transfer.

Figure 1:
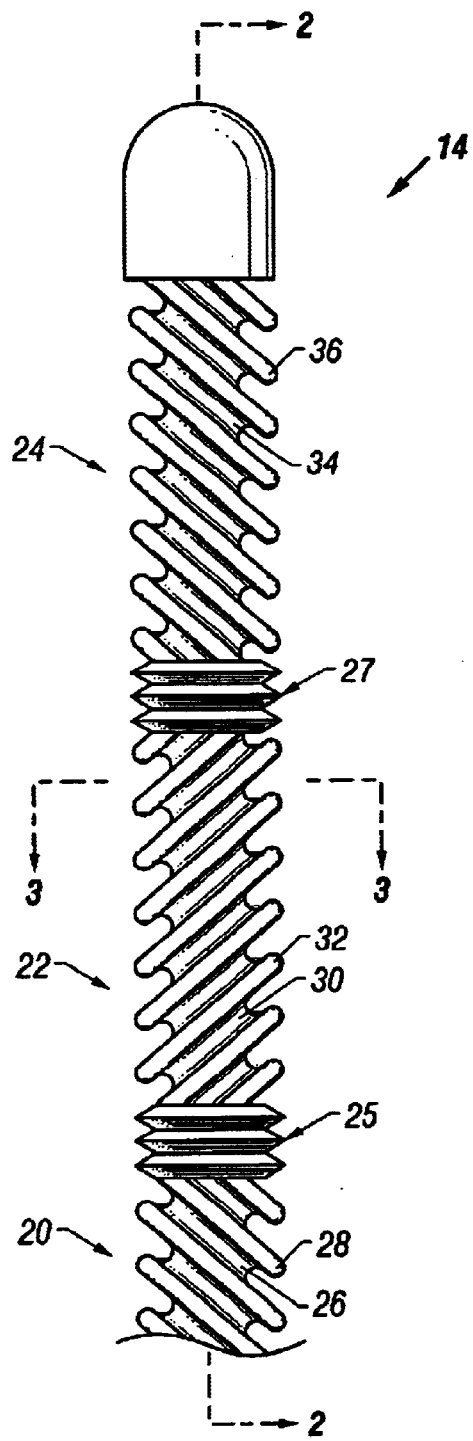
FIG. 1 is an elevation view of the one embodiment of a heat transfer element according to the invention.

FIG. 1 is an elevation view of one embodiment of a cooling element 14 according to the present invention. The heat transfer element 14 includes a series of elongated, articulated segments or modules 20, 22, 24. Three such segments are shown in this embodiment, but two or more such segments could be used without departing from the spirit of the invention. As seen in FIG. 1, a first elongated heat transfer segment 20 is located at the proximal end of the heat transfer element 14. A mixing-inducing exterior surface of the segment 20 includes four parallel helical ridges 28 with four parallel helical grooves 26 therebetween. One, two, three, or more parallel helical ridges 28 could also be used without departing from the spirit of the present invention. In this embodiment, the helical ridges 28 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first bellows section 25, which provides flexibility and compressibility. The second heat transfer segment 22 includes one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second bellows section 27. The third heat transfer segment 24 includes one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 28, 32, 36 allow the heat transfer element 14 to maintain a relatively atraumatic profile, thereby minimizing the possibility of damage to the blood vessel wall. A heat transfer element according to the present invention may include two, three, or more heat transfer segments.

The bellows sections 25, 27 are formed from seamless and nonporous materials, such as metal, and therefore are impermeable to gas, which can be particularly important, depending on the type of working fluid that is cycled through the heat transfer element 14. The structure of the bellows sections 25, 27 allows them to bend, extend and compress, which increases the flexibility of the heat transfer element 14 so that it is more readily able to navigate through blood vessels. The bellows sections 25, 27 also provide for axial compression of the heat transfer element 14, which can limit the trauma when the distal end of the heat transfer element 14 abuts a blood vessel wall. The bellows sections 25, 27 are also able to tolerate cryogenic temperatures without a loss of performance. In alternative embodiments, the bellows may be replaced by flexible polymer tubes, which are bonded between adjacent heat transfer segments.

The exterior surfaces of the heat transfer element 14 can be made from metal, and may include very high thermal conductivity materials such as nickel, thereby facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities, which is an important feature in a disposable medical device.

Because the heat transfer element 14 may dwell within the blood vessel for extended periods of time, such as 24–48 hours or even longer, it may be desirable to treat the surfaces of the heat transfer element 14 to avoid clot formation. In particular, one may wish to treat the bellows sections 25, 27 because stagnation of the blood flow may occur in the convolutions, thus allowing clots to form and cling to the surface to form a thrombus. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and thus prevent adherence of clotting factors. Another coating that provides beneficial properties may be a lubricious coating. Lubricious coatings, on both the heat transfer element and its associated catheter, allow for easier placement in the, e.g., vena cava.

Figures 2, 3:
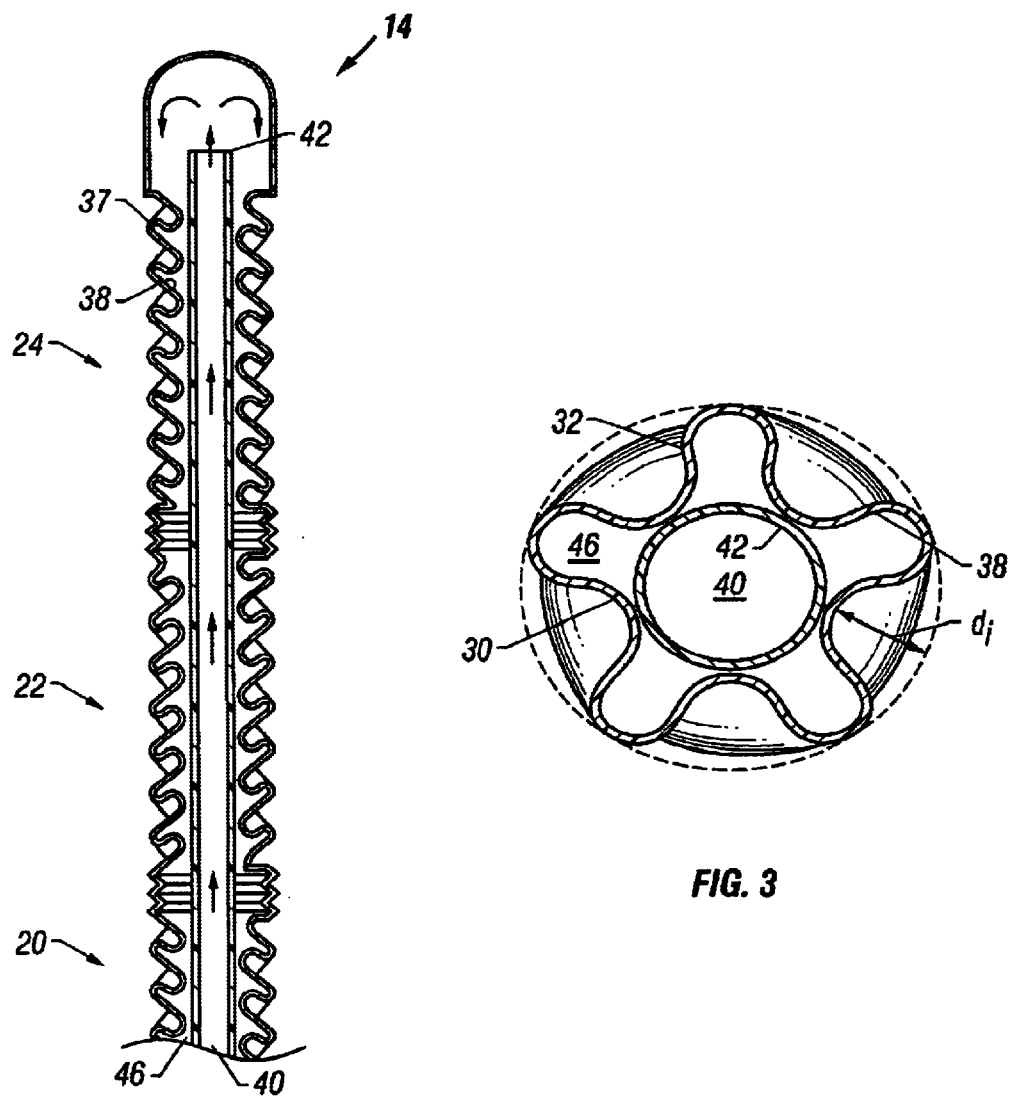
FIG. 2 is a longitudinal section view of the heat transfer element of FIG. 1.
FIG. 3 is a transverse section view of the heat transfer element of FIG. 1.

FIG. 2 is a longitudinal sectional view of the heat transfer element 14 of an embodiment of the invention, taken along line 2—2 in FIG. 1. Some interior contours are omitted for purposes of clarity. An inner tube 42 creates an inner lumen 40 and an outer lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner lumen 40. As the distal end of the heat transfer element 14, the working fluid exits the inner lumen 40 and enters the outer lumen 46. As the working fluid flows through the outer lumen 46, heat transfer from the working fluid to the exterior surface 37 of the heat transfer element 14. Because the heat transfer element 14 is constructed from a high conductivity material, the temperature of its exterior surface 37 may reach very close to the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or another polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid that remains a liquid as the working fluid. Other coolants such as Freon undergo nucleate boiling and create mixing through a different mechanism. Saline is a safe working fluid, because it is non-toxic, and leakage of saline does not result in a gas embolism, which could occur with the use of boiling refrigerants. Since mixing the working fluid is enhanced by the shape of the interior surface 38 of the heat transfer element 14, the working fluid can be delivered to the cooling element 14 at a warmer temperature and still achieve the necessary cooling rate. Similarly, since mixing in the working fluid is enhanced by the shape of the interior surface of the heat transfer element, the working fluid can be delivered to the warming element 14 at a cooler temperature and still achieve the necessary warming rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at a lower flow rates and lower pressures. High pressures may make the heat transfer element stiff and cause it to push against the wall of the blood vessel, thereby shielding part of the exterior surface 37 of the heat transfer element 14 from the blood. Because of the increased heat transfer characteristics achieved by the alternating helical ridges 28, 32, 36, the pressure of the working fluid may be as low as 5 atmospheres, 3 atmospheres, 2 atmospheres or even less than 1 atmosphere.

FIG. 3 is a transverse sectional view of the heat transfer element 14 of the invention, taken at a location denoted by the line 3—3 in FIG. 1. FIG. 3 illustrates a five-lobed embodiment, whereas FIG. 1 illustrates a four-lobed embodiment. As mentioned earlier any number of lobes might be used. In FIG. 3, the construction of the heat transfer element 14 is clearly shown. The inner lumen 40 is defined by the insulating tube 42. The outer lumen 46 is defined by the exterior surface of the insulating tube 42 and the interior surface 38 of the heat transfer element 14. In addition, the helical ridges 32 and helical grooves 30 may be seen in FIG. 3. Although FIG. 3 shows four ridges and four grooves, the number of ridges and grooves may vary. Thus, heat transfer elements with 1, 2, 3, 4, 5, 6, 7, 8 or more ridges are specifically contemplated.

Figure 4:
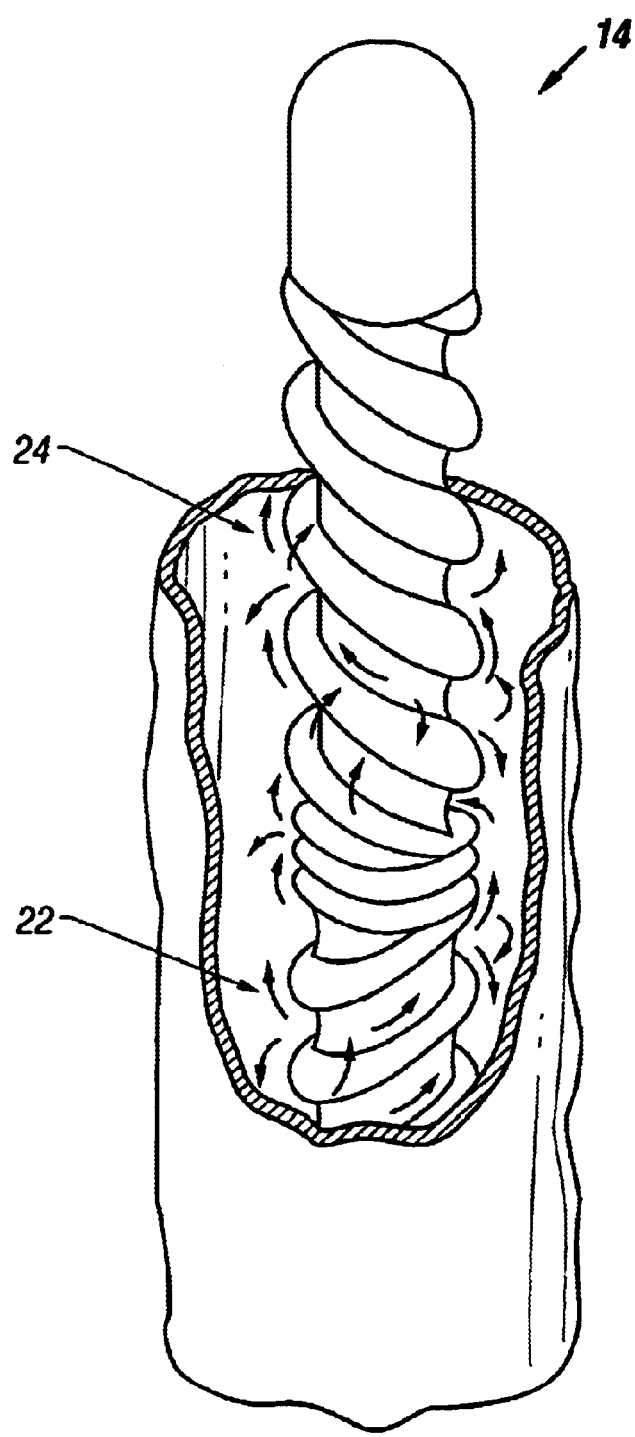
FIG. 4 is a perspective view of the heat transfer element of FIG. 1 in use within a blood vessel.

FIG. 4 is a perspective view of a heat transfer element 14 in use within the blood vessel, showing only one helical lobe per segment for purposes of clarity. Beginning from the proximal end of the heat transfer element (not shown in FIG. 4), as the blood moves forward, the first helical heat transfer segment 20 induces a counter-clockwise rotational inertia to the blood. As the blood reaches the second segment 22, the rotational direction of the inertia is reversed, causing mixing within the blood. Further, as the blood reaches the third segment 24, the rotational direction of the inertia is again reversed. The sudden changes in flow direction actively reorient and randomize the velocity vectors, thus ensuring mixing throughout the bloodstream. During such mixing, the velocity vectors of the blood become more random and, in some cases, become perpendicular to the axis of the vessel. Thus, a large portion of the volume of warm blood in the vessel is actively brought in contact with the heat transfer element 14, where it can be cooled by direct contact rather than being cooled largely by conduction through adjacent laminar layers of blood.

Referring back to FIG. 1, the heat transfer element 14 has been designed to address all of the design criteria discussed above. First, the heat transfer element 14 is flexible and is made of a highly conductive material. The flexibility is provided by a segmental distribution of bellows section 25, 27 that provide an articulating mechanism. Bellows have a known convoluted design that provide flexibility. Second, the exterior surface area 37 has been increased through the use of helical ridges 28, 32, 36 and helical grooves 26, 30, 34. The ridges also allow the heat transfer element 14 to maintain a relatively atraumatic profile, thereby minimizing the possibility of damage to the vessel wall. Third, the heat transfer element 14 has been designed to promote mixing both internally and externally. The modular or segmental design allows the direction of the grooves to be reverse between segments. The alternating helical rotations create an alternating flow that results in mixing the blood in a manner analogous to the mixing action created by the rotor of a washing machine that switches directions back and forth. This action is intended to promote mixing to enhance the heat transfer rate. The alternating helical design also causes beneficial missing, or turbulent kinetic energy, of the working fluid flowing internally.

Figure 5:
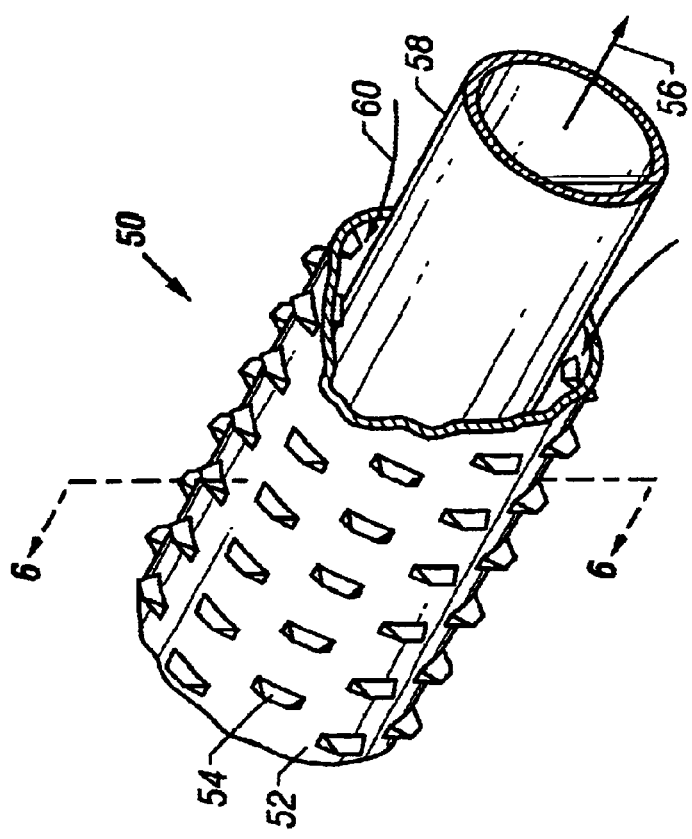
FIG. 5 is a cut-away perspective view of an alternative embodiment of a heat transfer element according to the invention.

FIG. 5 is a cut-away perspective view of an alternative embodiment of a heat transfer element 50. An external surface 52 of the heat transfer element 50 is covered with a series of axially staggered protrusions 54. The staggered nature of the outer protrusions 54 is readily seen with reference to FIG. 6 which is a transverse cross-sectional view taken at a location denoted by the line 6—6 in FIG. 5. As the blood flows along the external surface 52, it collides with one of the staggered protrusions 54 and a turbulent wake flow is created behind the protrusion. As the blood divides and swirls alongside of the first staggered protrusion 54, its turbulent wake encounters another staggered protrusion 54 within its path preventing the re-lamination of the flow and creating yet more mixing. In this way, the velocity vectors are randomized and mixing is created not only in the boundary layer but also throughout a large portion of the free stream. As is the case with the preferred embodiment, this geometry also induces a mixing effect on the internal working fluid flow.

Figure 6:
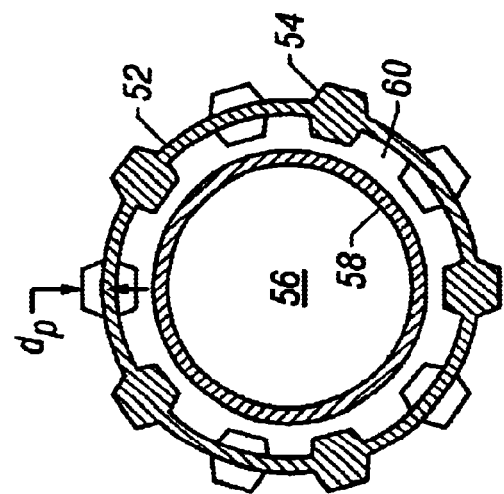
FIG. 6 is a transverse section view of the heat transfer element of FIG. 5.

A working fluid is circulated up through an inner lumen 56 defined by an insulating tube 58 to a distal tip of the heat transfer element 50. The working fluid then traverses an outer lumen 60 in order to transfer heat to the exterior surface 52 of the heat transfer element 50. The inside surface of the heat surface element 50 is similar to the exterior surface 52 in order to induce turbulent flow of the working fluid. The inner protrusions can be aligned with the outer protrusions 54 as shown in FIG. 6 or they can be offset from the outer protrusions 54 as shown in FIG. 5.

METHOD OF USE

Figure 7:
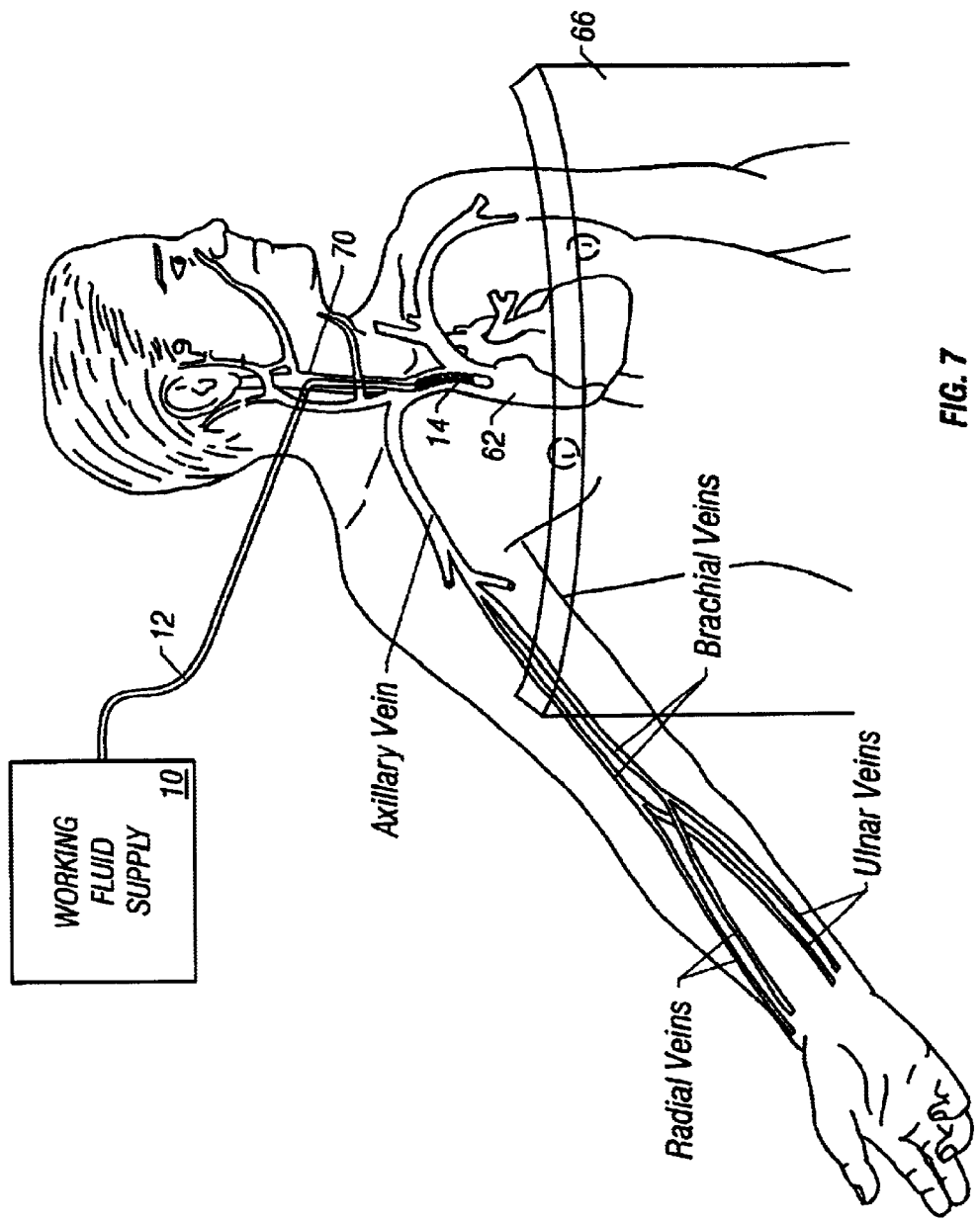
FIG. 7 is a schematic representation of the heat transfer element being used in one embodiment to provide hypothermia to a patient by causing total body cooling and then rewarming the body.

FIG. 7 is a schematic representation of the invention being use to cool the body of a patient and to warm a portion of the body. The hypothermia apparatus shown in FIG. 7 includes a first working fluid supply 10, preferably supplying a chilled liquid such as water, alcohol or a halogenated hydrocarbon, a first supply catheter 12 and the cooling element 14. The first supply catheter 12 may have a substantially coaxial construction. An inner lumen within the first supply catheter 12 receives coolant from the first working fluid supply 10. The coolant travels the length of the first supply catheter 12 to the cooling element 14 which serves as the cooling tip of the catheter. At the distal end of the cooling element 14, the coolant exits the insulated interior lumen and traverses the length of the cooling element 14 in order to decrease the temperature of the cooling element 14. The coolant then traverses an outer lumen of the first supply catheter 12 so that it may be disposed of or recirculated. The first supply catheter 12 is a flexible catheter having a diameter sufficiently small to allow its distal end to be inserted percutaneously into an accessible being such as the external jugular vein of a patient as shown in FIG. 7. The first supply catheter 12 is sufficiently long to allow the cooling element 14 at the distal end of the first supply catheter 12 to be passed through the vascular system of the patient and placed in the superior vena cava 62, inferior vena cava (not shown), or other such vein.

The method of inserting the catheter into the patient and routing the cooling element 14 into a selected vein is well know in the art. Percutaneous placement of the heat transfer element 14 into the jugular vein is accomplished directly, since the jugular vein is close to the surface. The catheter would reside in the internal jugular and into the superior vena cava or even the right atrium.

Although the working fluid supply 10 is shown as an exemplary cooling device, other devices and working fluids may be used. For example, in order to provide cooling, freon, perfluorocarbon, water, or saline may be used, as well as other such coolants.

The cooling element can absorb up to or more than 300 Watts of heat from the blood stream, resulting in absorption of as much as 100 Watts, 150 Watts, 170 Watts or more from the brain.

HEATING BLANKETS

FIG. 7 also shows a heating element 66, shown as a heating blanket. Heating blankets 66 generally are equipped with forced warm-air blowers that blow heated air through vents in the blanket in a direction towards the patient. This type of heating occurs through the surface area of the skin of the patient, and is partially dependent on the surface are extent of the patient. As shown in FIG. 7, the heating blanket 66 may cover most of the patient to warm and provide comfort to the patient. The heating blanket 66 need not cover the face and head of the patient in order that the patient may more easily breathe.

The heating blanket 66 serves several purposes. By warming the patient, vasoconstriction is avoided. The patient is also made more comfortable. For example, it is commonly agreed that for every one degree of core body temperature reduction, the patient will continue to feel comfortable if the same experiences a rise in surface area (skin) temperature of five degrees. Spasms due to total body hypothermia may be avoided. Temperature control of the patient may be more conveniently performed as the physician has another variable (the amount of heating) which may be adjusted.

As an alternative, the warming element may be any of the heating methods proposed in U.S. patent application Ser. No. 09/292,532, filed on Apr. 15, 1999, and entitled "Isolated Selective Organ Cooling Method and Apparatus", and incorporated by reference above.

The practice of the present invention is illustrated in the following non-limiting example.

Exemplary Procedure

1. The patient is initially assessed, resuscitated, and stabilized.
2. The procedure may be carried out in an angiography suite or surgical suite equipped with fluoroscopy.
3. An ultrasound or angiogram of the superior vena cava and external jugular can be used to determine the vessel diameter and the blood flow; a catheter with an appropriately sized heat transfer element can be selected.
5. After assessment of the veins, the patient is sterilely prepped and infiltrated with lidocaine at a region where the femoral artery may be accessed.
6. The external jugular is cannulated and a guide wire may be inserted to the superior vena cava. Placement of the guide wire is confirmed with fluoroscopy.
7. An angiographic catheter can be fed over the wire and contrast media injected into the vein to further to assess the anatomy if desired.
8. Alternatively, the external jugular is cannulated and a 10–12.5 french (f) introducer sheath is placed.
9. A guide catheter is placed into the superior vena cava. If a guide catheter is placed, it can be used to deliver contrast media directly to further assess anatomy.
10. The cooling catheter is placed into the superior vena cava via the guiding catheter or over the guidewire.
11. Placement is confirmed if desired with fluoroscopy.
12. Alternatively, the cooling catheter shaft has sufficient pushability and torqueability to be placed in the superior vena cava without the aid of a guide wire or guide catheter.
13. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
14. Cooling is initiated by starting the pump mechanism. The saline within the cooling catheter is circulated at 5 cc/sec. The saline travels through the heat exchanger in the chilled water bath and is cooled to approximately 1° C.
15. The saline subsequently enters the cooling catheter where it is delivered to the heat transfer element. The saline is warmed to approximately 5–7° C. as it travels along the inner lumen of the catheter shaft to the end of the heat transfer element.
16. The saline then flows back through the heat transfer element in contact with the inner metallic surface. The saline is further warmed in the heat transfer element to 12–15° C., and in the process, heat is absorbed from the blood, cooling the blood to 30° C. to 35° C. During this time, the patient may be warmed with an external heat source such as a heating blanket.
17. The chilled blood then goes on to chill the body. It is estimated that less than an hour will be required to cool the brain to 30° C. to 35° C.
18. The warmed saline travels back the outer lumen of the catheter shaft and is returned to the chilled water bath where the same is cooled to 1° C.
19. The pressure drops along the length of the circuit are estimated to be between 1 and 10 atmospheres.
20. The cooling can be adjusted by increasing or decreasing the flow rate of the saline. Monitoring of the temperature drop of the saline along the heat transfer element will allow the flow to be adjusted to maintain the desired cooling effect.
21. The catheter is left in place to provide cooling for, e.g., 6–48 hours.

Figure 8:
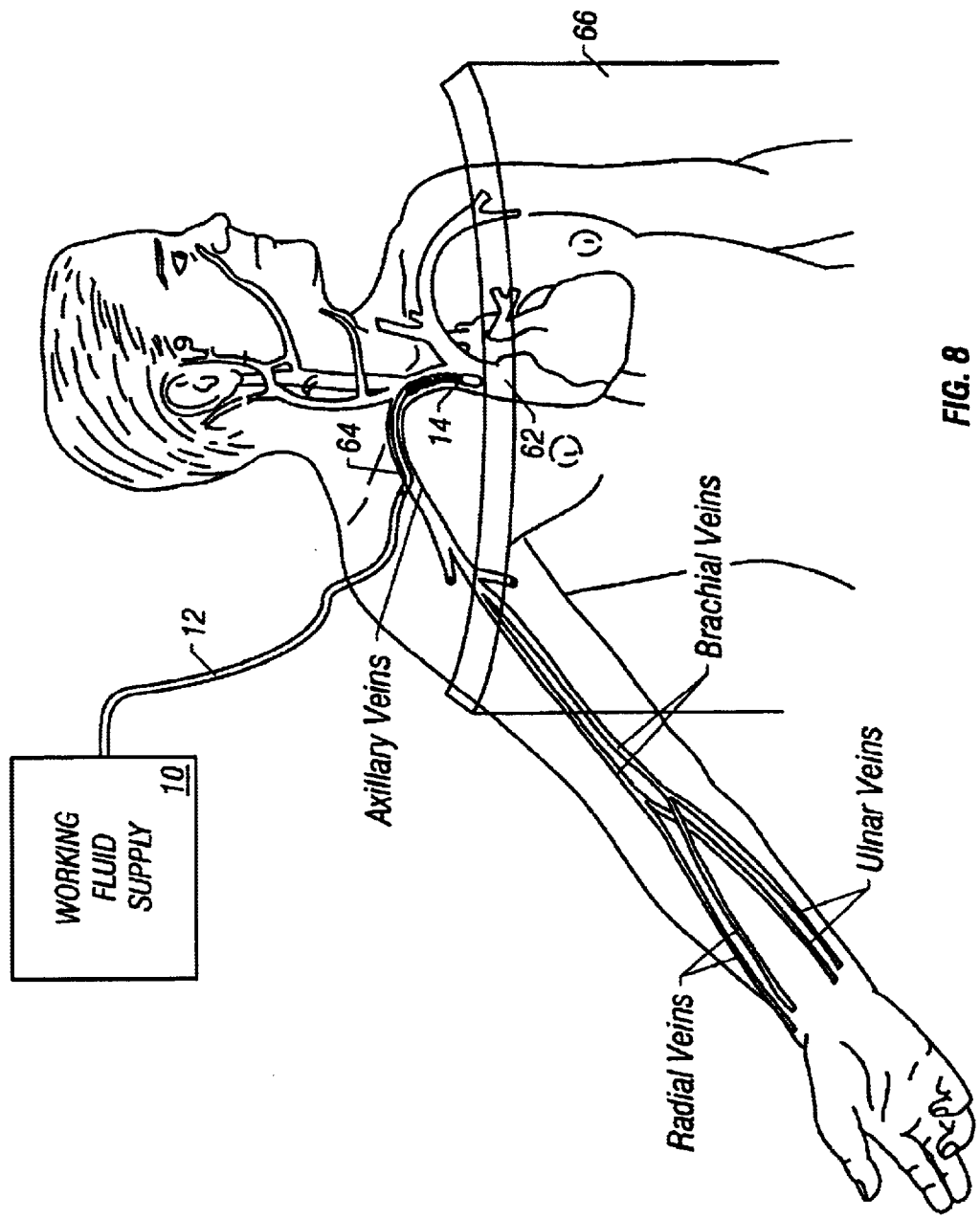
FIG. 8 is a schematic representation of the heat transfer element being used in another embodiment to provide hypothermia to a patient by causing total body cooling and then rewarming the body.

Referring to FIG. 8, an alternative embodiment is shown in which the heat transfer element 14 is disposed in the superior vena cava 62 from the axillary vein rather than from the external jugular. It is envisioned that the following veins may be appropriate to percutaneously insert the heat transfer element: femoral, internal jugular, subclavian, and other veins of similar size and position. It is also envisioned that the following veins may be appropriate in which to dispose the heat transfer element during use: inferior vena cava, superior vena cava, femoral, internal jugular, and other veins of similar size and position.

Figure 9:
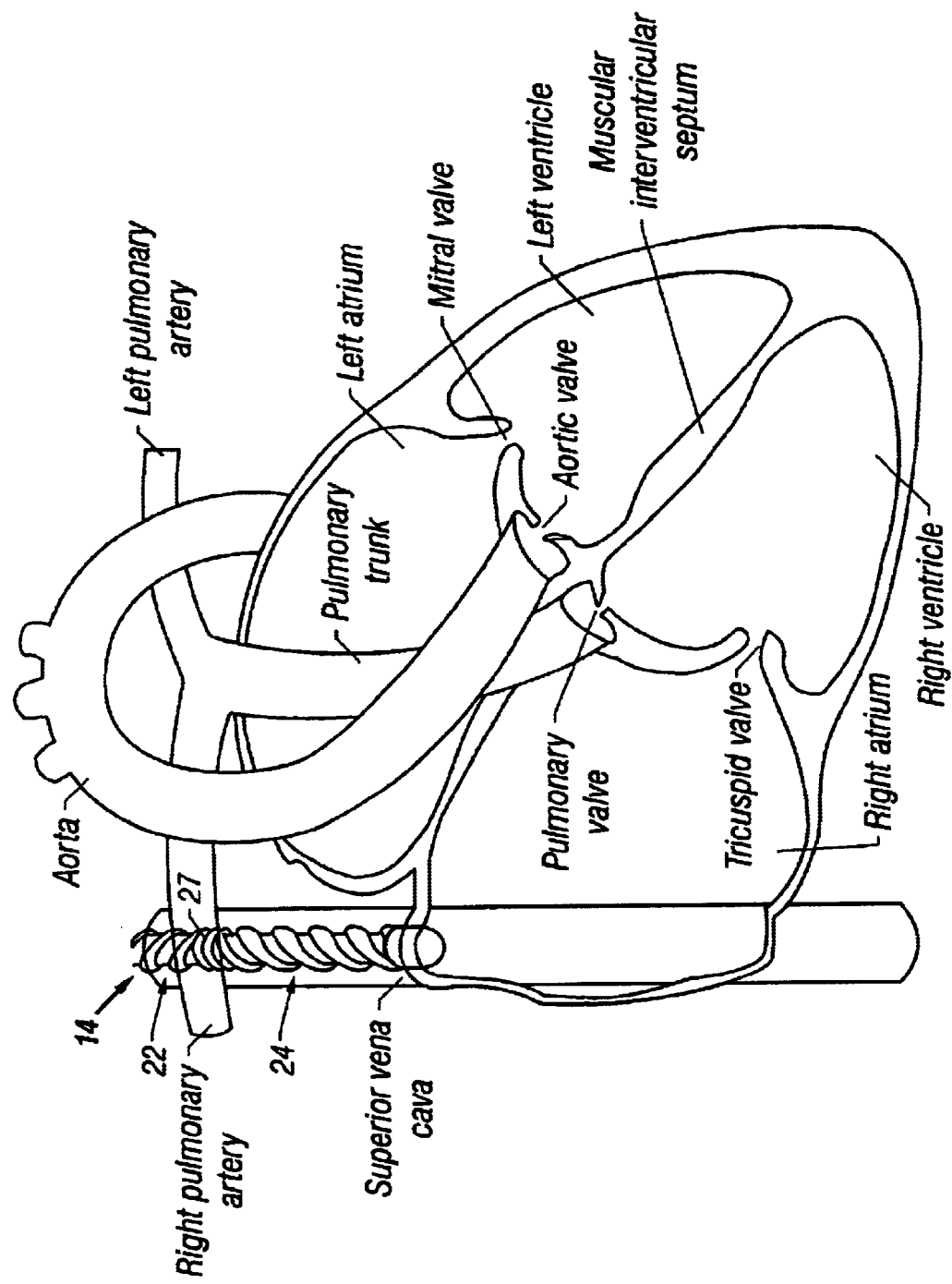
FIG. 9 is a schematic representation of the heat transfer element being used in an embodiment within the superior vena cava.

FIG. 9 shows a cross-section of the heart in which the heat transfer element 14 is disposed in the superior vena cava 62. The heat transfer element 14 has rotating helical grooves 22 as well as counter-rotating helical grooves 24. Between the rotating and the counter-rotating grooves are bellows 27. It is believed that a design of this nature would enhance the Nusselt number for the flow in the superior vena cava by about 5 to 80.

THERMOREGULATORY DRUGS

The above description discloses mechanical methods of rewarming a patient, or portions of a patient, to minimize the deleterious consequences of total body hypothermia. Another procedure which may be performed, either contemporaneous with or in place of mechanical warming, is the administration of anti-vasoconstriction and anti-shivering drugs. Such drugs minimize the effect of vasoconstriction which may otherwise hinder heated transfer and thus cooling of the patient. In general, hypothermia tends to trigger aggressive thermoregulatory defenses in the human body. Such drugs also prohibit responses such as shivering which may cause damage to cardiac-compromised patients by increasing their metabolic rate to dangerous levels.

To limit the effectiveness of thermoregulatory defenses during therapeutic hypothermia, drugs that induce thermoregulatory tolerance may be employed. A variety of these drugs have been discovered. For example, clonidine, meperidine, a combination of clonidine and meperidine, propofol, magnesium, dexmedetomidine, and other such drugs may be employed.

It is known that certain drug inhibit thermoregulation roughly in proportion to their anesthetic properties. Thus, volatile anesthetics (isoflurane, desflurane, etc.), propofol, etc. are more effective at inhibiting thermoregulation than opioids which are in turn more effective than midazolam and the central alpha agonsists. It is believed that the combination drug of clonidine and meperidine synergistically reduces vasoconstriction and shivering thresholds, synergistically reduces the gain and maximum intensity of vasoconstriction and shivering, and produces sufficient inhibition of thermoregulatory activity to permit central catheter-based cooling to 32° C. without excessive hypotension, autonomic nervous system activation, or sedation and respiratory compromise.

These drugs may be particularly important given the rapid onset of thermoregulatory defenses. For example, vasoconstriction may set in at temperatures of only ½ degree below normal body temperature. Shivering sets in only a fraction of a degree below vasoconstriction.

The temperature to which the blood is lowered may be such that thermoregulatory responses are not triggered. For example, thermoregulatory responses may be triggered at a temperature of 1–1½ degrees below normal temperature.

Thus, if normal body temperature is 37° C., thermoregulatory responses may set in at 35° C. Thermoregulatory drugs may used to lower the temperature of the thermoregulatory trigger threshold to 33° C. Use of the heating blankets described above may allow even further cooling of the patient. For example, to lower the patient's temperature from 33° C. to 31° C., a 2° C. temperature difference, a 2 times 5° C. or 10° C. rise is surface temperature may be employed on the skin of the patient to allow the patient to not "feel" the extra 2° C. coding.

Figure 11:
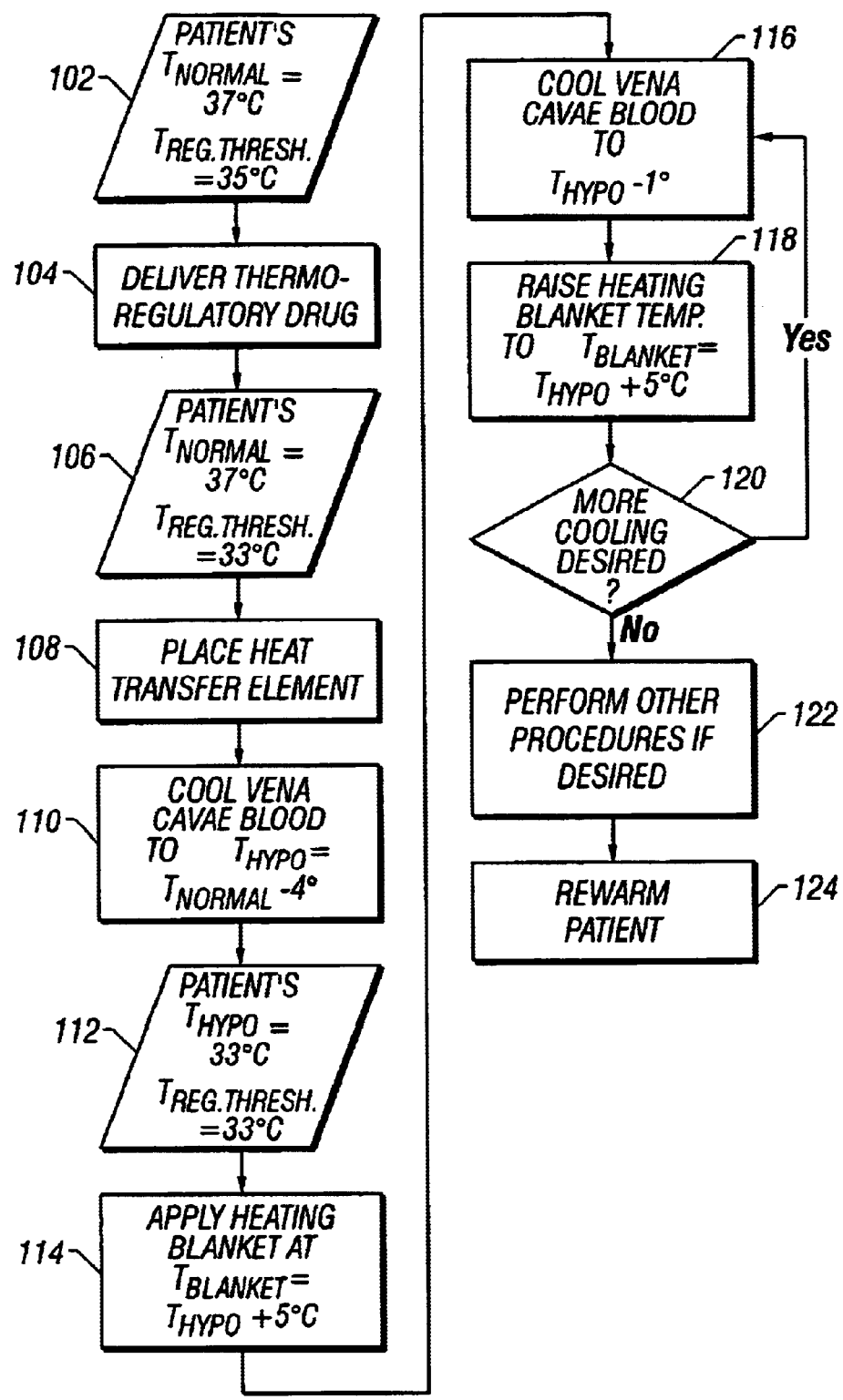
FIG. 11 is a flowchart showing an exemplary method of the invention employing heating blankets and thermoregulatory drugs.

A method which combines the thermoregulatory drugs methodology and the heating blanket methodology is described with respect to FIG. 11. This figure is purely exemplary. Patients' normal body temperatures vary, as do their thermoregulatory thresholds.

As shown in FIG. 11, the patient may start with a normal body temperature of 37° C. and a typical thermoregulatory threshold of 35° C. (step 102). In other words, at 35° C., the patient would begin to shiver and vasoconstrict. A thermoregulatory drug may be delivered (step 104) to suppress the thermoregulatory response, changing the threshold temperature to, e.g., 35° C. This new value is shown in step 106. The heat transfer element may then be placed in a high flow vein, such as the superior or inferior vena cavae or both (step 108). Cooling may occur to lower the temperature of the blood (step 110). The cooling may be in a fashion described in more detail above. The cooling results in the patient undergoing hypothermia and achieving a hypothermic temperature of, e.g., 33° C. (step 112). More cooling may be performed at this stage, but as the thermoregulatory threshold has only been suppressed to 33° C. (step 112), shivering and vasoconstriction would deleteriously result. This may complete the procedure. Alternatively, an additional drug therapy may be delivered to further lower the thermoregulatory threshold.

An alternate way to lower the thermoregulatory threshold is to use a heating blanket. As noted above, a common rule-of-thumb is that a patient's comfort will stay constant, even if their body temperature is lowered 1° C., so long as a heating blanket, 5° C. warmer than their skin, is applied to a substantial portion of the surface area of the patient (step 114). For a 2° C.-body temperature reduction, a 10° C. (warmer than the skin temperature) blanket would be applied. Of course, it is also known that blankets warmer than about 42° C. can damage patient's skins, this then being an upper limit to the blanket temperature. The patient's body temperature may then continue to be lowered by use of a heating blanket. For each 1° C. reduction in body temperature (step 116), the heating blanket temperature may be raised 5° C. (step 118). After each reduction in body temperature, the physician may decide whether or not to continue the cooling process (step 120). After cooling, other procedures may be performed if desired (step 122) and the patient may then be rewarmed (step 124).

It is important to note that the two alternate methods of thermoregulatory response reduction may be performed independently. In other words, either thermoregulatory drugs or heating blankets may be performed without the use of the other. The flowchart given in FIG. 11 may be used by omitting either step 104 or steps 114 and 118.

VASOCONSTRICTIVE THERAPIES

FIG. 10 showed the more rapid response of the high blood flow organs to hypothermia than that of the peripheral circulation. This response may be maintained or enhanced by applying, as an alternative method of performing hypothermia, a cooling blanket rather than a heating blanket. The cooling blanket may serve to vasoconstrict the vessels in the peripheral circulation, further directing blood flow towards the heart and brain.

An alternate method of performing the same function is to provide separate vasoconstrictive drugs which affect the posterior hypothalamus in such a way as to vasoconstrict the peripheral circulation while allowing heart and brain circulation to proceed unimpeded. Such drugs are known and include alpha receptor type drugs. These drugs, as well as the cooling blankets described above, may also enhance counter-current exchange, again forcing cooling towards the heart and brain. Generally, any drug or cooling blanket that provides sufficient cooling to initiate a large scale cutaneous peripheral vasoconstrictive response would be capable of forcing the cooling blood flow towards the brain and heart (i.e., the "central" volumes). In this application, the term "peripheral circulation" or "peripheral vasculature" refers to that portion of the vasculature serving the legs, arms, muscles, and skin.

ADDITIONAL THERAPIES

Turning now from thermoregulatory drugs to additional therapies, the method and device according to the embodiments of the invention may also play a significant role in treating a variety of maladies involving cell damage.

STROKE

A patent application incorporated by reference above discloses devices and methods for enhancing fibrinolysis of a clot by cooling blood flowing in an artery. The present invention may also use blood cooling to substantially reduce platelet aggregation as there is a significant reduction in platelet activity at reduced temperatures. Such reduction may take place by inhibiting enzyme function, although the actual methodology is unclear. This reduction in platelet aggregation, as well as the enhanced fibrinolysis noted above, may reduce or eliminate current dependence on such drugs as tPA or Rheopro.

MYOCARDIAL INFARCTION

The above-described venous cooling may also provide a number of benefits for patients undergoing myocardial infarction.

Current therapies for treating myocardial infarction involve three areas. Thrombolysis or stenting are used to establish reflow. The oxygen supply is increased by directly supplying the patient with oxygen and by vasodilation with nitrates. And the oxygen demand is lessened by decreasing the heart rate and the blood pressure.

Devices and methods according to the present invention can work well in combination with these current therapies. For example, the device and method may lessen the heart's demand for oxygen by providing cooled blood to the heart. The cooled blood in turn cools the inner chambers of heart, essentially from the inside. Hearts undergoing myocardial infarction may beat very fast due to an agitated state of the victim. However, cooled blood may induce a state of bradycardia that reduces the demand for oxygen by the heart per se.

To establish reflow and the oxygen supply, the enhanced fibrinolysis, discussed above, may also dissolve the clot, allowing more blood flow and more oxygen delivered to the heart. As mentioned above, platelet aggregation may be reduced. Additionally, conduction through the subendocardium, cooling the heart, may reduce the overall metabolic activity of the heart as well as protect the subendocardium from cell damage.

It is additionally noted that reflow is often accomplished by reperfusion injury which can further damage cells. Neutrophil activation occurs as part of reperfusion injury. Hypothermia can limit such activation and thus can limit reperfusion injury.

Thus, numerous therapies may be delivered by one device. Therefore, e.g., currently-employed "beta-blocker" drugs used to reduce heart rate in patients undergoing infarcts may not need to be employed in patients undergoing these hypothermic therapies.

RE-STENOSIS

Another application of the device and method may be in the treatment of stenotic arteries. Stenotic arteries are vessels that have narrowed due to a build-up of tissue and/or plaque atheroma. Stenotic vessels are treated by angioplasty or stenting, which opens the artery. During treatment the vessel wall may be injured. Such injuries often (20–50%) cause an inflammatory reaction that eventually causes the vessel to undergo re-stenosis after a period of time, which may range from 6–12 months or even several years later.

Hypothermia is known to mitigate inflammatory responses. For example, one of the initial steps in the process of re-stenosis is the migration of macrophagess or white blood cells to the injured area. Hypothermia can limit this migration. Hypothermia can also inhibit reactions and processes initiated by molecules acting in an autocrine or paracrine fashion. Hypothermia may also limit the release of several growth factors (at the site of injury) such as PDGF and EGF that act in these fashions.

While the invention herein disclosed is capable of obtaining the objects hereinbefore stated, it is to be understood that this disclosure is merely illustrative of the presently preferred embodiments of the invention and that no limitations are intended other than as described in the appended claims.

I claim:

1. A method for cooling a patient's body intravascularly, comprising:
   providing a catheter having a cooling element attached to a distal end thereof, the cooling element having mixing-inducing surface features thereon;
   inserting the catheter through the vascular system of the patient to place the cooling element in a vein that drains into the heart of a patient;
   circulating fluid through the cooling element;
   transferring heat from the blood in the vein to the cooling element; and
   administering an antishivering drug to the patient.

2. The method of claim 1, wherein the antishivering drug is selected from the group consisting of clonidine, meperidine, propofol, magnesium, dexmedetomidine, and combinations thereof.

3. The method of claim 1, wherein the cooling element is disposed in a vein selected from the group consisting of the superior vena cava, the inferior vena cava, the iliac vein, the femoral vein, or combinations of the above.

4. A method for changing a patient's body temperature intravascularly while controlling patient shivering, comprising:
   providing a catheter having a heat exchange element at a portion thereof;
   inserting the catheter through the vascular system of the patient to place the heat exchange element in a blood vessel;
   circulating fluid through the heat exchange element;
   transferring heat from the blood in the vessel to the heat exchange element; and
   administering an antishivering drug to the patient.

5. The method of claim 4, wherein the antishivering drug is selected from the group consisting of clonidine, meperidine, propofol, magnesium, dexmedetomidine, and combinations thereof.

6. A method for cooling a patient's body intravascularly, comprising:
   determining a target hypothermic temperature to be achieved;
   providing a catheter having a cooling element attached to a distal end thereof;
   inserting the catheter through the vascular system of the patient to place the cooling element in a vein that drains into the heart of a patient;
   circulating fluid through the cooling element;
   monitoring the patient temperature with a temperature probe;
   transferring heat from the blood in the vein to the cooling element and controlling the temperature of the patient so that the target temperature is substantially reached and so that the maximum temperature differential between the blood stream and the cooling element is limited to approximately 32° C.; and
   administering an antishivering drug to the patient.

7. The method of claim 6, further comprising inducing mixing in the blood stream.

8. The method of claim 6, wherein the antishivering drug is selected from the group consisting of clonidine, meperidine, propofol, magnesium, dexmedetomidine, and combinations thereof.

9. A method for cooling a patient's body intravascularly, comprising:
   providing a catheter having a cooling element attached to a distal end thereof, the cooling element having mixing-inducing surface features thereon;
   inserting the catheter through the vascular system of the patient to place the cooling element in a vein that drains into the heart of a patient;
   circulating fluid through the cooling element;
   transferring heat from the blood in the vein to the cooling element; and
   administering a thermoregulatory drug to the patient with the proviso that the thermoregulatory drug does not include vasodilatory drugs.

10. The method of claim 9, wherein the thermoregulatory drug is selected from the group consisting of clonidine, meperidine, propofol, magnesium, dexmedetomidine, and combinations thereof.

11. The method of claim 9, wherein the cooling element is disposed in a vein selected from the group consisting of the superior vena cava, the inferior vena cava, the iliac vein, the femoral vein, or combinations of the above.

12. A method for changing a patient's body temperature intravascularly while controlling patient shivering, comprising:
   providing a catheter having a heat exchange element at a portion thereof;
   inserting the catheter through the vascular system of the patient to place the heat exchange element in a blood vessel;
   circulating fluid through the heat exchange element;

transferring heat from the blood in the vessel to the heat exchange element; and administering a thermoregulatory drug to the patient with the proviso that the thermoregulatory drug does not include vasodilatory drugs.

13. The method of claim 12, wherein the thermoregulatory drug is selected from the group consisting of clonidine, meperidine, propofol, magnesium, dexmedetomidine, and combinations thereof.

14. A method for cooling a patient's body intravascularly, comprising:

determining a target hypothermic temperature to be achieved;

providing a catheter having a cooling element attached to a distal end thereof;

inserting the catheter through the vascular system of the patient to place the cooling element in a vein that drains into the heart of a patient;

circulating fluid through the cooling element;

monitoring the patient temperature with a temperature probe;

transferring heat from the blood in the vein to the cooling element and controlling the temperature of the patient so that the target temperature is substantially reached and so that the maximum temperature differential between the blood stream and the cooling element is limited to approximately 32° C.; and administering a thermoregulatory drug to the patient with the proviso that the thermoregulatory drug does not include vasodilatory drugs.

15. The method of claim 14, further comprising inducing mixing in the blood stream.

16. The method of claim 14, wherein the thermoregulatory drug is selected from the group consisting of clonidine, meperdine, propofol, magnesium, dexmedetomidine, and combinations thereof.

* * * * *